United States Patent [19]
Fischell et al.

[11] Patent Number: 5,176,617
[45] Date of Patent: * Jan. 5, 1993

[54] USE OF A STENT WITH THE CAPABILITY TO INHIBIT MALIGNANT GROWTH IN A VESSEL SUCH AS A BILIARY DUCT

[75] Inventors: Robert E. Fischell, Dayton, Md.; Tim A. Fischell, Los Altos, Calif.

[73] Assignee: Medical Innovative Technologies R & D Limited Partnership, Dayton, Md.

[*] Notice: The portion of the term of this patent subsequent to Oct. 22, 2008 has been disclaimed.

[21] Appl. No.: 779,641

[22] Filed: Oct. 21, 1991

Related U.S. Application Data

[63] Continuation-in-part of Ser. No. 448,691, Dec. 11, 1989, Pat. No. 5,059,166.

[51] Int. Cl.⁵ ............................................. A61N 5/00
[52] U.S. Cl. ............................................. 600/3; 600/12; 424/1.1
[58] Field of Search ............... 600/1, 3, 12; 606/108, 606/139; 128/11, 804, 899; 424/1.1

[56] References Cited

U.S. PATENT DOCUMENTS 5,059,166 10/1991 Fischell et al. ...................... 600/12

Primary Examiner—Lee S. Cohen
Assistant Examiner—J. P. Lacyk

[57] ABSTRACT

It is well known that radiation therapy can reduce the proliferation of rapidly growing cancer cells is a malignant tumor. The present invention utilizes a radioisotope which is integral to a stent which can irradiate the tissue in close proximity to the implantation site of the stent in order to reduce the rapid growth of malignant cells in a vessel, such as a bile duct while simultaneously maintaining vessel patency. The radioisotope could be place inside the stent, alloyed into the metal from which the stent is made, or preferably, it can be coated onto the stent's exterior surface.

11 Claims, 1 Drawing Sheet

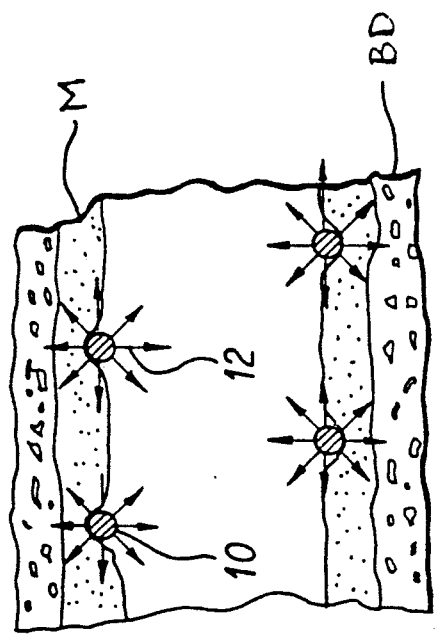
FIG. 1
FIG. 2
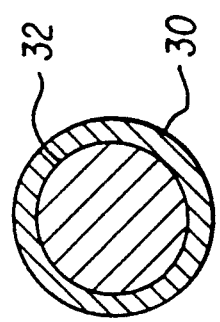
FIG. 3

USE OF A STENT WITH THE CAPABILITY TO INHIBIT MALIGNANT GROWTH IN A VESSEL SUCH AS A BILIARY DUCT

This application is a continuation-in-part of application Ser. No. 07/448,691, filed Dec. 11, 1989 now U.S. Pat. No. 5,059,166.

This invention is in the field of cancer treatment, specifically, a new method to open a vessel of the human body while simultaneously decreasing the growth rate of malignant cells in that vessel, such as the bile duct and thereby maintain its patency.

BACKGROUND OF THE INVENTION

Since the mid-to-late-1980s, intra-arterial stents have found extensive use as a treatment to prevent restenosis subsequent to balloon angioplasty or atherectomy. A recurrent problem is that excessive tissue growth (intimal hyperplasia) at the site of the balloon dilation or atherectomy plaque excision results in restenosis of the artery. One possible solution to this problem is to coat the stent with an anti-thrombogenic surface so as to reduce platelet and fibrin deposition. This is described in U.S. Pat. No. 4,768,507 issued Sep. 1988, to Robert E. Fischell and Tim A. Fischell entitled "Intravascular Stent and Percutaneous Insertion Catheter System for the Dilation of an Arterial Stenosis and the Prevention of Restenosis" which is incorporated herein by reference. Although an anti-thrombogenic coating can prevent acute thrombotic arterial closure and decrease the need for anticoagulant drug therapy, there is still an urgent need to decrease restenosis which is caused by intimal hyperplasia. Similarly, stents have been used in the bile duct of patients with liver cancer to maintain duct patency. However, malignant cells soon grow through the stent and close the bile duct or severely impede its function.

SUMMARY OF THE INVENTION

It is well known that radiation therapy can reduce the proliferation of rapidly growing cancer cells in a malignant tumor. The present invention utilizes a radioisotope which is integral to a stent which can irradiate the tissue in close proximity to the implantation site of the stent in order to reduce the rapid malignant cell growth in a vessel, such as a bile duct while simultaneously maintaining vessel patency.

BRIEF DESCRIPTION OF THE DRAWINGS

FIG. 1 is a cross section showing two turns of a radioisotope helical coil spring stent imbedded into a human vessel, such as the bile duct.

FIG. 2 is a cross section through the spring wire of a helical coil spring stent showing a radioisotope core material within a spring material.

FIG. 3 is a cross section through the spring wire of a helical coil spring stent showing a thin plating of radioisotope material on the exterior surface.

DETAILED DESCRIPTION OF THE DRAWINGS

As described in U.S. Pat. No. 4,768,507, intra-arterial stents can be made in the form of a deployable helical coil spring. FIGS. 5 and 6 of the U.S. Pat. No. 4,768,507, illustrate typical cross sections of such a spring wire, helical coil stent.

FIG. 1 of the present invention shows a cross section 10 of two turns of a helical coil spring stent that has been fabricated from a pure metal or alloy which has been irradiated so that it has become radioactive; i.e., it is a radioisotope. These two turns are shown imbedded into malignant cells (M) in bile duct (BD). The arrows 12 pointing outward from the cross section 10 indicate the omnidirectional emission of particles from the stent wire. The purpose of this radiation is to decrease the rate of malignant cell growth of the bile duct (BD). Thus it would be expected that closure of the bile duct, which frequently occurs after stent implantation, will be significantly reduced.

The radioisotope used for this purpose may be an alpha, beta or gamma emitter. The half-life would ideally be between 10 hours and 1000 days. An optimum emitter might be a beta emitting isotope such as vanadium 48 which has a half-life of 16 days and only 8% of its emitted energy is from gamma radiation. The ideal attribute of a beta emitter is that the radiation does not travel very far in human tissue. Thus only the tissue in close proximity to the radioisotope stent will be affected. Furthermore only moderate levels of radiation are desired since it is known that very high levels can cause injury to nonproliferating tissues.

Another method to make the material of the stent spring wire is from a metal into which is alloyed an element that can be made into a radioisotope. For example, phosphorus 32, a 14.3 day half-life beta emitter, could be alloyed into steel which could be used for the stent wire.

FIG. 2 shows a stent wire cross section in which a wire made from a radioisotope core material 20 is formed within an outer covering 22 that has the attributes that are desirable for being a coil spring stent.

FIG. 3 shows a cross section of an alternative embodiment of the present invention in which a radioisotope coating 30 is plated onto a spring material core 32. For example, the beta emitting isotope gold 198 (half-life 2.7 days) could be used to coat any suitable spring metal material.

Although helical coil spring stents have generally been described herein, the concept of utilizing a radioactive material within the stent's structure so to attenuate malignant cell growth in a vessel, such as a bile duct is certainly applicable to any stent design. Furthermore, the temporary placement at the site of the bile duct of a radioactive source within the lumen of the bile duct, for example a thin wire with a radioactive tip which wire can be withdrawn after a limited time, is also envisioned.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent comprising a generally tubular structure whose external surface is adapted to engage the wall of a human vessel, said stent being patent throughout its entire interior length and being formed from a radioactive material which is outwardly, radially expandable after insertion into a vessel of the human body, the radioactive material being adapted to be imbedded into the vessel wall so that the radioactive material preferentially emits radiation that can reduce the proliferation of malignant cells in the vessel wall that are in close proximity to said stent while simultaneously maintaining vessel patency.

2. The stent of claim 1 in which the radioactive material emitting the radiation is a radioisotope.

3. The stent of claim 2 in which said radioisotope is integrally formed within the structural material of said generally tubular structure of the stent.

4. The stent of claim 2 in which said radioisotope is plated onto said generally tubular structure of the stent.

5. The stent of claim 2 in which said radioisotope is a beta particle emitting radioisotope.

6. A stent comprising a generally tubular, thin-walled structure adapted to be expanded radially outward against the wall of a vessel in a human body at least part of said stent being formed from a radioisotope material which is radially expandable, said radioisotope material being adapted to be imbedded into the vessel wall and further being adapted to decrease the rate of growth of the malignant cells while simultaneously maintaining vessel patency.

7. The stent of claim 6 in which said radioisotope has a half-life of less than 1000 days.

8. A method to simultaneously decrease growth of malignant cells in a vessel of a living body while maintaining vessel patency the method comprising:
   insertion of an expandable stent into the vessel, at least part of said stent being formed from a radioisotope material.

9. The method of claim 8 wherein said stent is inserted into a bile duct.

10. The method of claim 8 further comprising the step of excising at least some of the malignant tissue in the bile duct by means of an atherectomy catheter prior to insertion of the stent.

11. A method to simultaneously decrease growth of malignant cells in a vessel of a living body while maintaining vessel patency the method comprising:
   percutaneous insertion of a radioisotope source into a vessel by means of a catheter so that it is positioned at the site of the malignant cells, said radioisotope source being formed from a plurality of thin, wire-like, interconnected, radially expandable parts in the form of an expandable stent;
   radially expanding the radioisotope source so that it becomes imbedded in the vessel; and,
   removal of the catheter from the artery.

* * * * *